United States Patent
Green

(10) Patent No.: US 6,239,123 B1
(45) Date of Patent: *May 29, 2001

(54) USE OF ESTROGENIC COMPOUNDS AS ANTI-FUNGAL AGENTS

(75) Inventor: Shawn J. Green, Vienna, VA (US)

(73) Assignee: Entremed, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/371,585

(22) Filed: Aug. 10, 1999

Related U.S. Application Data

(60) Provisional application No. 60/096,145, filed on Aug. 11, 1998.

(51) Int. Cl.$^7$ ..................................................... A61K 31/56
(52) U.S. Cl. ............................................................ 514/182
(58) Field of Search ............................................. 514/182

(56) References Cited

U.S. PATENT DOCUMENTS 5,962,445 * 10/1999 Stewart ................................ 514/182

FOREIGN PATENT DOCUMENTS

WO 99/35150    7/1999 (WO).

OTHER PUBLICATIONS

Refai, M et al.; Castellania (Berlin) (1974), 2(11), 257–60; Studies on the effect of some hormones on *Candida albicans* and *Cryptococcus neoformans* in vitro and in vivo.*

Refai, M. et al., "Studies on the effect of some hormones on Candida albicans and Cryptococcus neoformans in vitro and in vivo", Castellania (Berlin) (1974), 2(11), pp. 257–260.

Loose, D.S., Schurman, D.J., Feldman, D., "A Corticosteroid binding protein and endogenous ligand in *C. albicans* indicating a possible steroid–receptor system", Oct. 8, 1981, vol. 293, pp. 477–479.

Larsen, B., Galask, R.P., "Influence of Estrogen and Normal Flora on Vaginal Candidiasis in the Rat", Dec. 8, 1984, vol. 29, No. 12, pp. 863–868.

Brem, H., et al., "Interstitial chemotherapy with drug polymer implants for the treatment of recurrent gliomas", J. Neurosurg, Mar. 6, 1991, vol. 74, pp. 441–446.

Zhao, X., et al., "Oestrogen–binding protein in *Candida albicans* : antibody development and cellular localization by electron immunocytochemistry", Microbiology, Oct. 1995, 141, pp. 2685–2692.

Gujjar, P.R. Finucane, M., Larsen, B., "The Effect of Estradiol in *Candida albicans* Growth", Annals of Clinical and Laboratory Science, vol, 27, No. 2, pp. 151–156.

Cushman, M., et al., "Synthesis of Analogs of 2–Methoxyestradiol with Enhanced Inhibitory Effects on Tubulin Polymerization and Cancer Cell Growth", Journal of Medicinal Chemistry, Jul. 1997, vol. 40, No. 15, pp. 2323–2334.

White,S., and Larsen, B., "*Candida albicans* morphogenesis is influenced by estrogen", CMLS, Cell. mol. life sci. 53 (1997), Birkhauser Verlag, CH–4010 Basel Switzerland, pp. 744–749.

* cited by examiner

*Primary Examiner*—Theodore J. Criares
*Assistant Examiner*—Jennifer Kim
(74) *Attorney, Agent, or Firm*—Kilpatrick Stockton LLP

(57) ABSTRACT

The present invention provides compounds that are useful for inhibiting the proliferation of fungi. The compounds are estrogenic derivatives, such as 2ME2, or anti-estrogenic compounds. The compounds may be used for treating infections of fungi in humans and animals, or to prevent or inhibit the growth of fungi on any surface.

8 Claims, 1 Drawing Sheet

USE OF ESTROGENIC COMPOUNDS AS ANTI-FUNGAL AGENTS

This application claims priority to provisional application U.S. Ser. No. 60/096,145 filed Aug. 11, 1998.

FIELD OF THE INVENTION

This invention relates to the treatment of fungal infections with estrogenic derivatives.

BACKGROUND OF THE INVENTION

Candidiasis is a fungal infection of mucosal membranes and other tissues. The infection is caused by the yeast-like organism Candida. Numerous species of Candida exist, including C. albicans. The recent increase in candidiasis is most likely caused by the rising incidence of AIDS, more intensive regimens of cancer therapy, complications of abdominal or cardio-thoracic surgery, organ transplantations, burns and trauma. Immunocompromised individuals and women of childbearing age, especially pregnant women or women with one or more child births, are known to be more susceptible to microbial pathogenesis. Alteration of the fungi microenvironment is currently considered to be accountable for the initiation of C. albicans infection symptoms (1). Changes in pH, temperature, osmotic pressure, and hormonal concentrations are some of the environmental factors that induce virulence expression.

While most candidiasis patients are infected with C. albicans, the number of non-C. albicans infections has been growing steadily and may reflect the increased use of azole drug prophylaxis and therapy since some non-C. albicans species are innately resistant to these drugs. Additional risk factors commonly associated with the onset of candidiasis include protracted, broad-spectrum antibiotic therapies, invasive devices, and prolonged hospital stays. Under these conditions, an antibiotic resistant replacement flora, including one or more fungal species, can proliferate in the gastrointestinal tract and invade from mucosal foci to deep tissues, especially when mucosal integrity has been disrupted as a result of chemotherapy or surgery.

2-Methoxyestradiol (2ME2), an end product of 17$\beta$-estradiol metabolism, is a well-known anti-mitogen that suppresses the growth of rapidly dividing mammalian cells by interfering with the progression of their cell cycle. Although a number of studies have been published regarding the effects of 2ME2 and related derivatives on the proliferation of endothelial and tumor cells, nothing is known about the effects of this metabolite on the replication of non-mammalian cells.

Recently, 17$\beta$-estradiol has emerged as one of the agents that support C. albicans germination and growth (1, 2). Specifically, growth of yeast cells in serum stripped of any steroid compound (by means of activated charcoal) results in reduction of the percentage of germinating cells, and thus, in reduction in virulence. Supplementation of the stripped media with exogenous estradiol in nanomolar concentrations restores germination. This property is specific to 17$\beta$-estradiol, since cholesterol and the $\alpha$-isomer of estradiol do not induce morphogenic changes in C. albicans. In addition, certain strains of C. albicans require the presence of 17$\beta$- or 17$\beta$-estradiol for rapid growth.

The importance of estrogen as a virulence factor is also reinforced by in vivo studies in which estrogen treatment is required to induce susceptibility of oophorectomized to vaginal colonization of C. albicans (3, 4), and the presence of an estrogen-binding protein (EBP) in C. albicans that binds to estrogen with high affinity and specificity (5, 6).

SUMMARY OF THE INVENTION

The present invention provides compounds that are useful for inhibiting the growth of fungi. The compounds are estrogenic derivatives, such as 2ME2, and analogs thereof. The compounds may be used for treating infections of fungi in humans and animals, or to prevent or inhibit the growth of fungi on any surface. Furthermore, the invention contemplates the use of anti-estrogenic compounds, such as tamoxifen and raloxifen, as anti-fungal treatments.

DETAILED DESCRIPTION OF THE INVENTION

Figure 1:
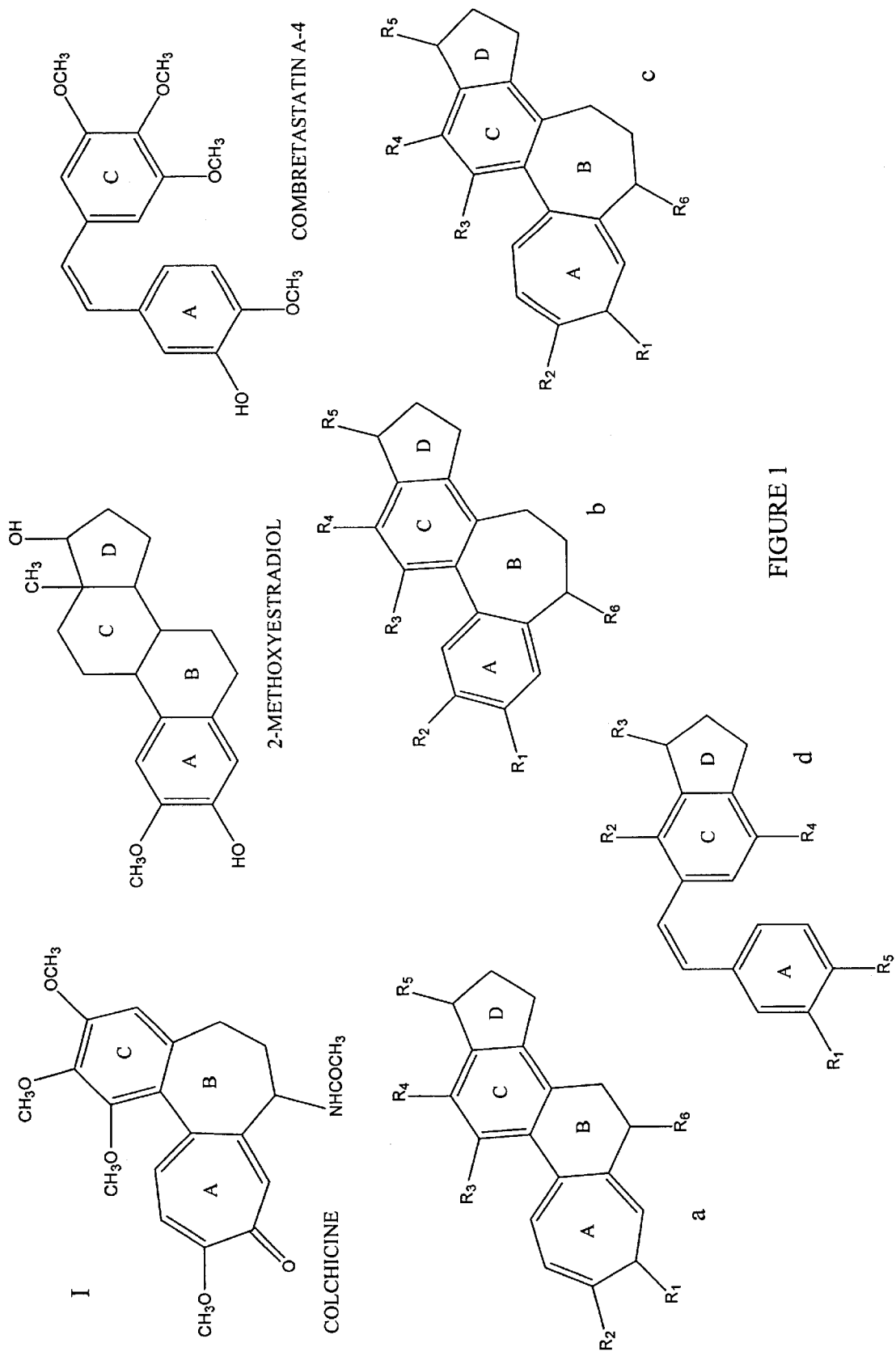
FIG. 1 shows the chemical structure of 2-methoxyestradiol, and the molecular formulae of colchicine, combretastatin A-4, and other estradiol derivatives.

As described below, compounds that are useful in accordance with the invention include estradiol derivatives that inhibit fungal growth, including the growth of yeasts and filamentous fungi. The present invention provides that estrogenic derivatives can be used as a fungi-static agent in humans and animals, as well as on any fungal-contaminated surface.

Specific compounds according to the invention are described below, such as 2-methoxyestradiol (2ME2), shown in FIG. 1. Those skilled in the art will appreciate that the invention extends to other derivatives of estrogens and estradiols, having the described characteristics. Examples of other estrogenic derivatives and analogs contemplated herein may be found in U.S. Pat. No. 5,661,143, which is incorporated by reference in its entirety. Given the present discovery that 2ME2 is a fungi-static agent, these characteristics can be determined for each estrogenic derivative and analog using the assays detailed below and known to those skilled in the art.

The invention provides that certain estrogenic derivatives, such as 2ME2, antagonize the stimulatory actions of other estrogens, such as 17$\beta$-estradiol, on the replication of yeast cells. The invention also provides for the use of anti-estrogenic compounds, such as tamoxifen and raloxifen, as anti-fungal treatments to inhibit the growth stimulatory effect of certain estrogens. Many other anti-estrogenic compounds are well-known in the art.

Further, the invention provides that certain estrogenic derivatives, such as 2ME2, reverse resistance to common antifungal treatments. The administration of estrogenic derivatives, e.g. 2ME2, either alone or in combination with other anti-fungals, e.g. azoles, provides a new method for treatment of fungal infections, such as candidiasis.

Synthesis of Estrogenic Derivatives

The synthesis of the estrogenic derivatives described herein is well within the capability of one ordinarily skilled in the art. A specific description of the synthesis of the 2-ME derivatives and analogs contemplated herein can be found in Cushman, et al. Synthesis, antitubulin and antimitotic activity, and cytotoxicity of 2-methoxyestradiol, and endogenous mammalian metabolite of estradiol that inhibits tubulin polymerization by binding to the colchicine binding site, J. Med. Chem., 38(12): 2042 (1995); and Cushman, et al. Synthesis of analogs of 2-methoxyestradiol with enhanced inhibitory effects on tubulin polymerization and cancer cell growth, J. Med. Chem. 40(15): 2323 (1997).

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, DA. *Helv. Chim. Acta.* 63, 1703, (1980)). Synthetic methods for making seven-membered rings in multi-cyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index*, 11th Ed., Merck & Co., Inc., Rahway, N.J. USA (1989), pp. 583–584).

FIG. 1 illustrates the molecular formulae of colchicine, 2-methoxyestradiol, combretastatin A-4, and other estradiol derivatives. Molecular formulae are drawn and oriented to emphasize structural similarities between the ring structures of colchicine, combretastatin A-4, estradiol, and certain estradiol derivatives. Estradiol derivatives can be made by incorporating colchicine or combretastatin A-4 structural motifs into the steroidal backbone of estradiol. FIG. 1, part I, depicts the chemical formulae of colchicine, 2-methoxyestradiol and combretastatin A-4. FIG. 1, part II a–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 1, may be fully saturated as found in 2-methoxyestradiol. $R_{1-6}$ represent a subset of the substitution groups found in the claims. Each $R_1$–$R_6$ can independently be defined as —$R_1$, $OR_1$, —$OCOR_{11}$—$SR_1$, —F, —$NHR_2$, —Br, —I, or —C≡CH.

Particularly preferred estradiol derivatives, in addition to 2-methoxyestradiol, that have anti-fungal activity are among those represented by the formula:

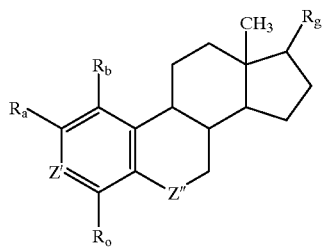

wherein:
a) $R_b$ and $R_o$ are independently —H, —Cl, —Br, —I, —F, —CN, lower alkyl, —OH, —$CH_2$—OH, —$NH_2$; or $N(R_6)(R_7)$, wherein $R_6$ and $R_7$ are independently hydrogen or an alkyl or branched alkyl with up to 6 carbons;
b) $R_a$ is —$N_3$, —C≡N, —$N_3$, —C≡C—R, —C=CH—R, —R—C=$CH_2$, —C=CH, —O—R, —R—$R_1$, or —O—R—$R_1$ where R is a straight or branched alkyl with up to 10 carbons or aralkyl, and $R_1$ is —OH, —$NH_2$, —Cl, —Br, —I, —F or $CF_3$;
c) Z' is >CH, >COH, or >C—$R_2$—OH, where $R_2$ is an alkyl or branched alkyl with up to 10 carbons or aralkyl;
d) >C—$R_g$ is >$CH_2$, >C(H)—OH, >C=O, >C=N—OH, >C($R_3$)OH, >C=N—$OR_3$, >C(H)—$NH_2$, >C(H)—$NHR_3$, >C(H)—$NR_3R_4$, or >C(H)—C(O)—$R_3$, where each $R_3$ and $R_4$ is independently an alkyl or branched alkyl with up to 10 carbons or aralkyl; and
e) Z" is >$CH_2$, >C=O, >C(H)—OH, >C=N—OH, >C=N—$OR_5$, >C(H)—C≡N, or >C(H)—$NR_5R_5$, wherein each $R_5$ is independently hydrogen, an alkyl or branched alkyl with up to 10 carbons or aralkyl.

Anti-fungal Activity

Anti-fungal activity is evaluated by testing the ability of an estrogen derivative, or anti-estrogenic compound, to inhibit the growth of fungal species. A suitable assay is found in the following examples and in the literature. Using such an assay, an estrogenic derivative, or anti-estrogenic compound, is added to a fungal culture and observed for the ability to inhibit fungal growth after a time period. This result indicates that the estrogenic derivative, or anti-estrogenic compound, can inhibit fungal growth.

Indications

The invention can be used to treat any disease characterized by fungal infection. Such diseases include, but are not limited to candidiasis and thrush. The invention may also be used to prevent the growth of fungal species on inanimate objects, such as hospital equipment.

Administration

The compositions described above can be provided as physiologically acceptable formulations using known techniques, and these formulations can be administered by standard routes. In general, the combinations may be administered by the topical, oral, vaginal, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991). The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

The invention may be further appreciated by the following non-limiting examples, which are intended to be demonstrative of certain embodiments of the invention.

EXAMPLE 1

The ability of 3 $\mu$M 2ME2 to inhibit the growth of ten different strains of *C. albicans* was investigated. Nine of these strains were clinically isolated and maintained by interval of subculture with Sabouraouds dextrose agar and storage at 4° C.; the other strain was purchased from ATCC. Yeast cells were cultured with nitrogen broth devoid of mammalian steroid hormones in the presence and absence of 2ME2. At 5 and 12 hours after the addition of 2ME2, a small volume of control and treated cultures was drawn and plated on Sabouraouds dextrose agar plates. The plates were placed at 37° C. and the colonies counted 24 hours later. Table I illustrates that micromolar concentrations 2ME2 are able to suppress the growth of 9/10 strains of *C. albicans* tested here.

TABLE I

| Strain | Number of Control Colonies at 5 hrs | Number of Treated Colonies at 5 hrs | Number of Control Colonies at 12 hrs | Number of Treated Colonies at 12 hrs | Percentage of Inhibition at 12 hrs |
|---|---|---|---|---|---|
| ATCC | 17 | 15 | 221 | 67 | 70% |
| 1 | 15 | 16 | 254 | 50 | 57% |
| 2 | 61 | 51 | >400 | >400 | 0 |
| 3 | 16 | 14 | >400 | 86 | >78% |
| 4 | 13 | 17 | >400 | 113 | >72% |
| 5 | 34 | 14 | >400 | 85 | >79% |
| 6 | 51 | 32 | >400 | 131 | >67% |
| 7 | 22 | 13 | >400 | 148 | >63% |
| 8 | 23 | 14 | >400 | 98 | >75% |
| 9 | 21 | 15 | >400 | 90 | >77% |

EXAMPLE 2

The experiment described in Example 1 was repeated with 4 of the above strains and 3 newly isolated *C. albicans* strains. The following counts were taken from yeast cultures grown for 5 hours in the nitrogen base media in the presence and absence of micromolar concentrations 2ME2.

TABLE II

| Strain | Control Colonies | Treated Colonies | Percentage of Inhibition |
|---|---|---|---|
| 10 | 50 ± 2 | 51 ± 19 | 0% |
| 8 | 118 ± 12 | 59 ± 7 | 50% |
| 11 | 86 ± 6 | 74 ± 16 | 14% |
| ATCC | 64 ± 3 | 36 ± 6 | 44% |
| 2 | 88 ± 5 | 26 ± 7 | 70% |
| 12 | 155 | 77 ± 12 | 50% |
| 5 | 99 ± 7 | 58 ± 7 | 41% |

EXAMPLE 3

In a separate experiment, 1 nM 17$\beta$-estradiol was added to the cultures of *C. albicans* cells in the presence and absence of 1 $\mu$M 2ME2 and the number of colonies of yeast cells cultured for 5 hours with the above steroids were counted as previously described. Table III shows the data.

TABLE III

| Strain | Number of Colonies treated with estradiol | Number of Colonies treated with estradiol and 2ME$_2$ | Percentage of Inhibition |
|---|---|---|---|
| 10 | 52 ± 2 | 23 ± 5 | 56% |
| 8 | 48 ± 7 | 25 ± 3 | 48% |
| 11 | 80 ± 1 | 55 ± 6 | 31% |
| ATCC | 63 ± 8 | 28 ± 12 | 55% |
| 2 | 58 ± 5 | 64 ± 2 | 0 |
| 12 | 120 | 56 ± 1 | 53% |
| 5 | 69 ± 13 | 39 ± 4 | 43% |

References

1. P. R. Gujjar, M. Finucane, and B. Larsen. The effect of Estradiol and *Candida albicans* Growth. Ann Clin Lab Sci, 27(2): 151–156 (1997).
2. S. White and B. Larsen. *Candida albicans* morphogenesis is influenced by estrogen. Cell Mol Life Sci, 53(9): 744–749 (1997).
3. B. Larsen and R. P. Galask. Influence of estrogen and normal flora on vaginal candidiasis in the rat. J. Reprod Med, 29: 863–868 (1984).
4. A. Cassone, F. De Bernadis, G. Santoni, D. Adriani, and M. Boccanera. Rats clearing a vaginal infection by *Candida albicans* acquire specific, antibody-mediated resistance to vaginal reinfection.
5. D. S. Loose, D. J. Schurman, and D. Feldman. A corticosteroid binding protein and endogenous ligand in *Candida albicans* indicating a possible steroid receptor system. Nature, 293: 477–479 (1981).
6. X. Zhao, D. Feldman, C. M. Ardies, and P. J. Malloy. Oestrogen-binding protein in *Candida albicans*: antibody development and cellular localization by electron immunohistrochemistry. Microbiology, 141: 2685–92 (1995).

All of the publications mentioned herein are hereby incorporated by reference in their entireties. The above examples are merely demonstrative of the present invention, and are not intended to limit the scope of the appended claims.

I claim:

1. A method of inhibiting the proliferation of a fungus, comprising administering to the fungus a proliferation inhibiting amount of a 2-methoxyestradiol.

2. The method of claim 1, wherein the fungus is a Candida species.

3. A method of treating a fungal infection in an individual, comprising administering to the individual a fungal infection-treatment effective amount of a 2-methoxyestradiol.

4. The method of claim 3, wherein the fungal infection is candidiasis.

5. The method of claim 3, wherein the individual is a mammal.

6. The method of claim 3, wherein the individual is a human.

7. The method of claim 2, wherein the Candida species is *Candida albicans*.

8. The method of claim 4, wherein the individual is infected with *Candida albicans*.

* * * * *